United States Patent [19]

Dondlinger

[11] Patent Number: 5,249,679
[45] Date of Patent: Oct. 5, 1993

[54] MEDICAL NEEDLE DISPOSAL PACKAGE

[76] Inventor: Steven C. Dondlinger, 5513 Knoll Dr., Edina, Minn. 55436

[21] Appl. No.: 878,298

[22] Filed: May 6, 1992

[51] Int. Cl.$^5$ .......................... A61L 2/16; B65F 1/00; B65D 85/24
[52] U.S. Cl. ................................... 206/366; 206/365; 206/813; 220/8
[58] Field of Search .................... 206/366, 365, 813; 220/8

[56] References Cited

U.S. PATENT DOCUMENTS

| | | | |
|---|---|---|---|
| 3,973,356 | 8/1976 | Schacht | 220/8 |
| 4,748,125 | 5/1988 | Pizzolante | 206/813 |
| 4,936,449 | 6/1990 | Conard et al. | 206/366 |
| 5,046,613 | 9/1991 | Baudry et al. | 206/365 |
| 5,092,462 | 3/1992 | Sagstetter et al. | 206/366 |

Primary Examiner—William I. Price
Attorney, Agent, or Firm—Hugh D. Jaeger

[57] ABSTRACT

A medical needle disposal package for disposing of needles, such as surgical needles, IV needles, syringe needles, lancets, and other like sharp surgical devices. A package with hard sides, a hard bottom and sticky tape on the bottom and/or sides, contains STYROFOAM-like material. The used surgical needles or devices are stuck into the STYROFOAM. The package provides that a needle can be stuck into the STYROFOAM with one hand. At a latter time, the package and needles are disposed of by accepted surgical waste disposal procedures. The package can also be provided with an engagable top.

1 Claim, 2 Drawing Sheets

MEDICAL NEEDLE DISPOSAL PACKAGE

BACKGROUND OF THE INVENTION

1. Field of the Invention

The present invention pertains to a disposable medical package, and more particularly, pertains to a disposable medical package for engaging of surgical needles or surgical instruments for later disposal.

2. Description of the Prior Art

Prior art problems of disposal of needles have been that the needles are left lying on trays, such as IV trays, causing accidental sticks, which then exposes an individual to the AIDS virus or other infectious organisms.

Further, disposing of needles has been a two-hand operation of trying to insert the needle back into the cap, and this has always been of concern of accidental sticks which exposes one to the AIDS virus or other infectious organisms, and also, used needles have either been left lying in the open or stuck into other objects, such as mattresses.

The present invention overcomes the disadvantages of the prior art by providing a one-handed needle disposal process and safe location for used needles, such as on disposable trays.

SUMMARY OF THE INVENTION

The general purpose of the present invention is a medical needle disposal package for storing of used needles and later disposal of used needles.

According to one embodiment of the present invention, there is provided a medical needle disposal package, including a block of STYROFOAM surrounded by hard sides and a hard bottom. A top can be provided for engaging onto the package for later disposition of the package. Appropriate locking members can also be provided, providing that the package cannot be reopened for any reason, so as to protect the environment. The package and the contents could then be either incinerated or disposed of at a sanitary landfill. A sticky material can be provided on the bottom or about the sides of the disposal package for engaging on an IV tray or other suitable medical table or medical appliance, further providing for one-handed operation of disposing of needles into the package.

Significant aspects and features of the present invention include a medical needle disposal package which provides a soft, cellular type of material, such as STYROFOAM, which needles or other surgical devices can be easily pushed in to and also readily retained within the material.

Another significant aspect and feature of the present invention is a medical needle disposal package with STYROFOAM which provides for one-handed operation.

A further significant aspect and feature of the present invention is a medical disposal package for needles or like surgical instruments, which can be disposed of either through incineration, sanitary landfill, or other suitable processes.

Having thus described the embodiments of the present invention, it is a principal object hereof to provide a medical needle disposal package.

One object of the present invention is to provide a medical needle disposal package to prevent accidental sticks and potential exposure to the AIDS virus or other infectious organisms.

Another object of the present invention is to provide a medical needle disposal package which provides for one-handed operation and is economical enough to be at all sites of all needle or instrument usage which could possibly cause an accidental stick or cut, exposing one to the AIDS virus or other infectious organisms.

A further object of the present invention is a medical disposal package which serves the purpose to reduce medical waste, such as reducing sharp boxes.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
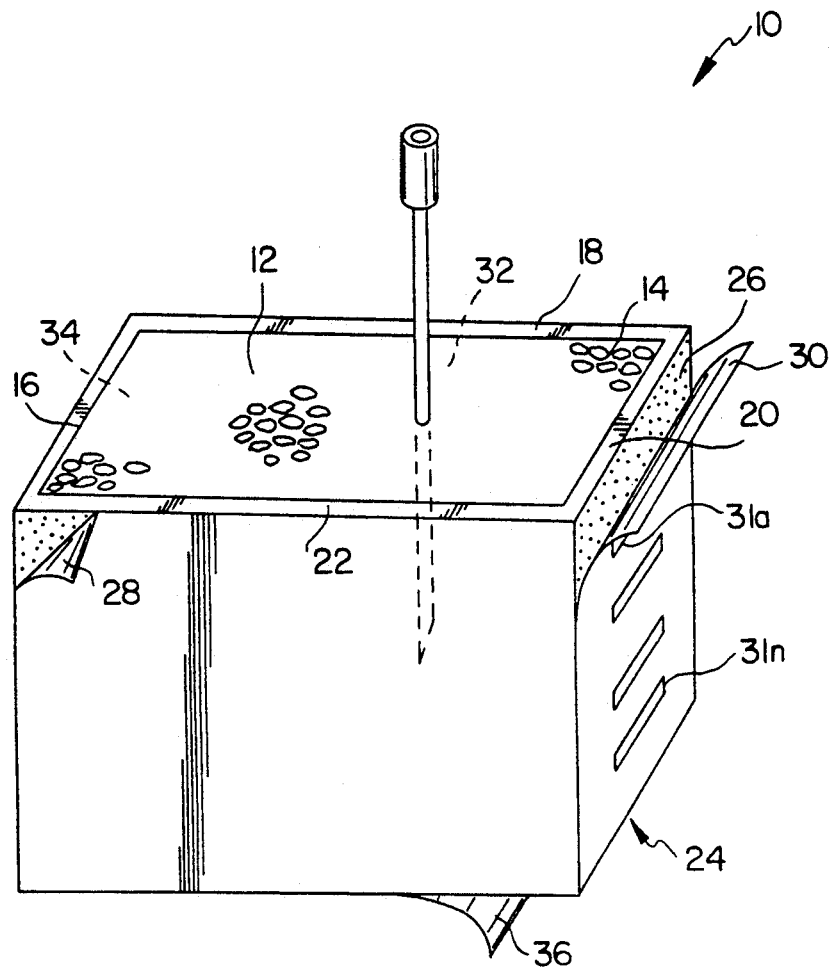
FIG. 1 illustrates the medical needle disposal package and a needle engaged within the package.

FIG. 1 illustrates a perspective view of a medical needle disposal package 10 including a block or like member 12 of soft or pliable cellular material, such as STYROFOAM 14, by way of example and for purposes of illustration only and not to be construed as limiting of the present invention, engaged by four hard sides 16, 18, 20 and 22, and a bottom 24. Other materials, such as polystyrenes, polyurethanes or any other suitable polymers, which would functionally engage a needle in a firm position In this view the sides 16-22 and the bottom 24 are coated with an adhesive 26, or in the alternative, are covered with a double-sided adhesive tape or the like, one side of which adheres to the sides 16-22 and the bottom 24. Protective peel-away sheets 28, 30, 32, 34 and 36 overlay the adhesive on the sides 16-22 and the bottom 24, and are peeled away as illustrated so that one or more of the planar surfaces of the sides 16-22 and the bottom 24 can be adhesively secured to a surgical table or tray.

Figure 2:
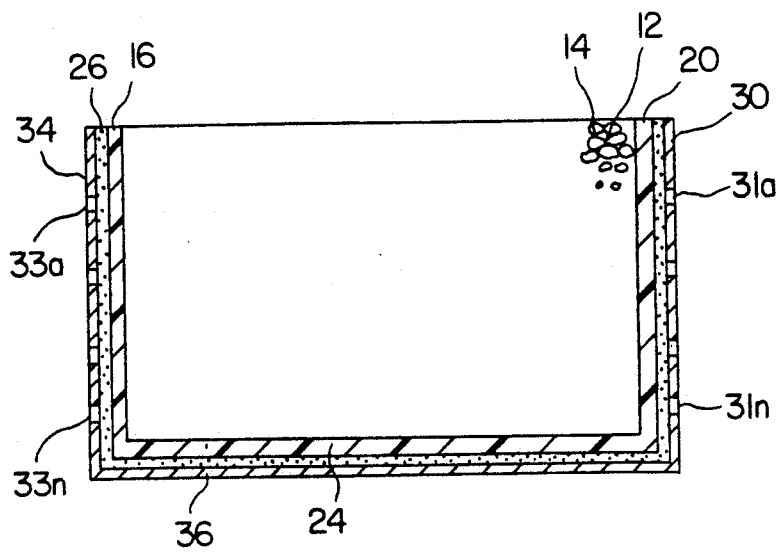
FIG. 2 illustrates a conceptual side view.

FIG. 2 illustrates a conceptual side view in cross section of FIG. 1 where all numerals correspond to those elements previously described.

MODE OF OPERATION

Figure 3:
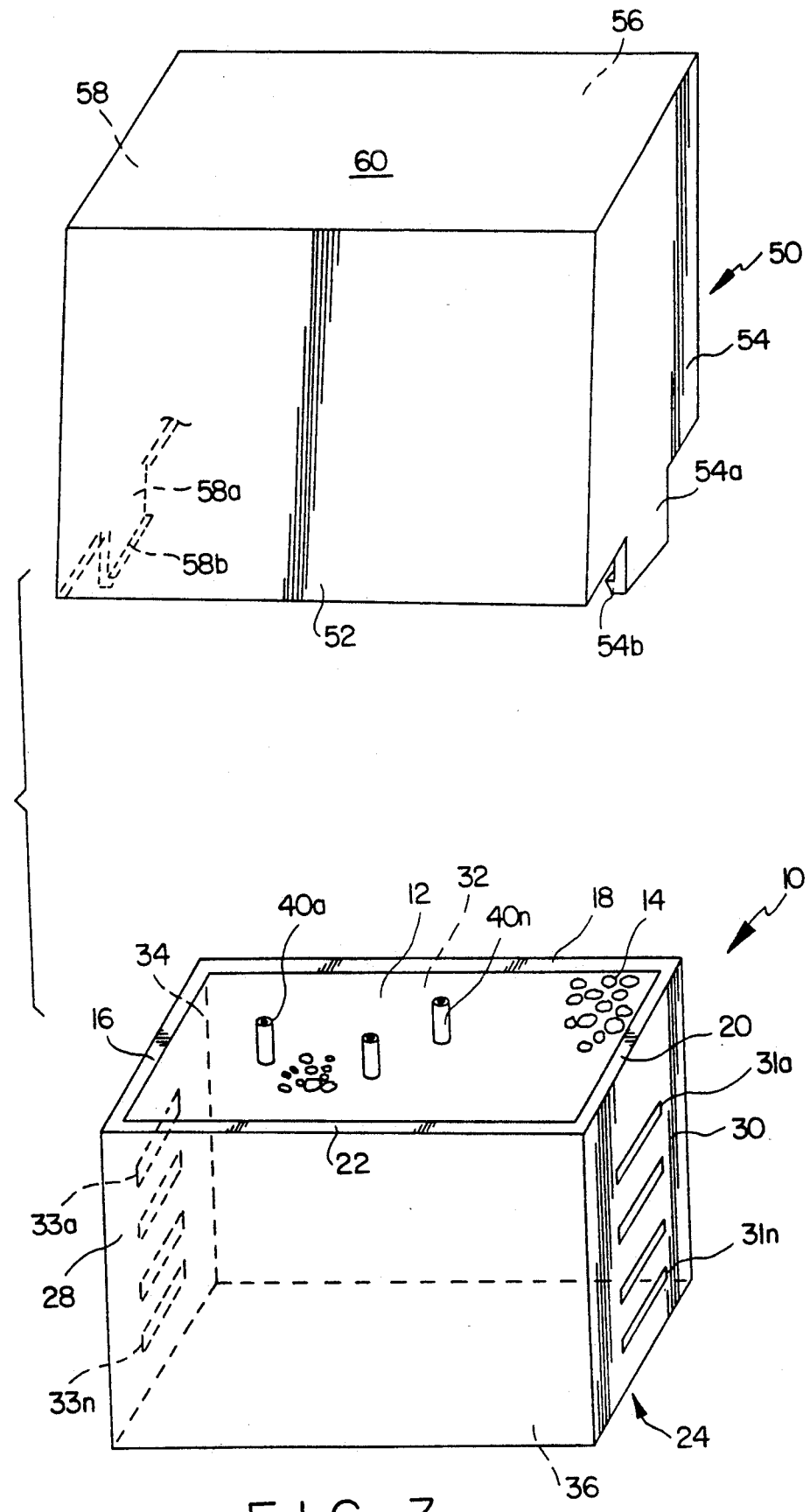
FIG. 3 illustrates an optional top for engagement to a package with needles for disposal.

FIG. 3 illustrates a plurality of needles 40a-40n engaged into the STYROFOAM 14 in the package 10. A plurality of needles can be placed into the package 10 until either one makes a decision to dispose of the package, or in the alternative, the package is full of needles and can no longer accommodate any other needles for disposition. An optional top 50 with four hard sides 52, 54, 56, 58, and a hard top 60 can be engaged over the package 10 and snapped into position so that the bottom and top cannot be separated at a later time. Sides 58 and 54 include extension members 58a and 54a extending downwardly and having locking tab members 58b and 54b located respectively at the lower edges to engage corresponding latching groove members contained in a plurality of latching grooves 31a-31n on side 20 and a plurality of latching grooves 33a-33n on side 16. Cutouts in the double-sided sticky tape and associated peel-away coverings align with the latching grooves 31a–31n and 33a–33n to accommodate the locking tab members 54b and 58b. The extension members 54a and 58a can also extend beyond the plurality of latching grooves 31a–31n and 33a–33n and snappingly engage the lower edge of sides 16 and 20 to lock the top 50 over and about the top portion of the medical needle disposal package 10. The use of pluralities of latching grooves allows the package 10 and top 50 to accommodate needles or other sharp surgical devices of varying heights.

Engaging locks or clips can be alternatively provided internally for the package top and bottom for engaging with respect to each other.

The package 10 can later be disposed by accepted contaminated surgical waste procedures, such as incinerators or landfills.

Various modifications can be made to the present invention without departing from the apparent scope hereof.

I claim:

1. A medical apparatus disposable package comprising:
   a. a lower member;
   b. said lower member including a soft cellular material for acceptance of medical apparatus surrounded by hard sides and a hard bottom;
   c. said lower member including an adhesive substance on a portion of its outer surface with a protective peel-away member thereover;
   d. said lower member having a plurality of opposing latch members on at least two opposing sides, each of said plurality of opposing latch members on each opposing side being vertically spaced with respect to each other, each member of which aligns with a corresponding rectangular hole in said peel-away protective member, whereby said adhesive material allows said lower member to be adhesively attached to a surgical tray or other surface, thereby allowing one-handed disposal of used medical apparatus;
   e. an upper member including upper member hard sides, a hard top, side extensions and opposing locking tab members configured to engage said opposing latch members to seal contents of said lower member between said upper and lower members, the particular opposing latch members engaged being a function of the height of said medical apparatus being disposed.

* * * * *